(12) United States Patent
Rea

(10) Patent No.: US 7,379,767 B2
(45) Date of Patent: May 27, 2008

(54) ATTACHABLE AND SIZE ADJUSTABLE SURFACE ELECTRODE FOR LARYNGEAL ELECTROMYOGRAPHY

(76) Inventor: James Lee Rea, 662 Bismark Ave., Ventura, CA (US) 93004

( * ) Notice: Subject to any disclaimer, the term of this patent is extended or adjusted under 35 U.S.C. 154(b) by 221 days.

(21) Appl. No.: 11/324,484

(22) Filed: Jan. 3, 2006

(65) Prior Publication Data

US 2007/0156041 A1    Jul. 5, 2007

(51) Int. Cl.
*A61B 5/04* (2006.01)
(52) U.S. Cl. .................. 600/380; 600/373; 600/546
(58) Field of Classification Search ................. 600/380
See application file for complete search history.

(56) References Cited

U.S. PATENT DOCUMENTS 4,890,623 A * 1/1990 Cook et al. ................. 600/374

5,343,860 A * 9/1994 Metzger et al. ............. 600/380

* cited by examiner

*Primary Examiner*—Lee S Cohen
(74) *Attorney, Agent, or Firm*—Richard Grundstrom

(57) ABSTRACT

An electrode for laryngeal electromyography that is attachable to an insert device, endotracheal tune or other similar device that is also size adjustable by cutting to size. The attachable and size adjustable surface electrode of this invention consists of a flexible plate having an anterior and a posterior surface specifically for inserting in the human laryngopharynx adjacent to the cricothyroideus muscles (the vocal cords). An electrical conductive plate is mounted on the anterior surface to provide an electric contact with the cricothyroideus muscles. An insulated wire extends from the electrical conductive plate for monitoring or delivering electrical pulses to the cricothyroideus muscles. There are marked graduations parallel to a center line on the electrical conductive plate for cutting and sizing the flexible plate and electrical conductive plate to the size of the patient's laryngopharynx. There is an adhesive material on the posterior surface of the flexible plate for attachment of the attachable and size adjustable surface electrode for laryngeal electromyography to an endotracheal tube, insert device, postcricoid paddle or other such device.

5 Claims, 4 Drawing Sheets

ATTACHABLE AND SIZE ADJUSTABLE SURFACE ELECTRODE FOR LARYNGEAL ELECTROMYOGRAPHY

BACKGROUND OF THE INVENTION

This invention relates to electrodes for laryngeal electromyography and in particular to an electrode that is attachable to an insert device of sorts and that is size adjustable to fit the particular application, and in particular for use in pediatrics.

During thyroid surgery there is a substantial hazard that the recurrent laryngeal nerve may be severed, stretched or bruised during surgery on, about or near the thyroid gland. The hazard is a result of several factors, including the fact that the recurrent laryngeal nerve lies just posterior to the most inferior portion of the thyroid gland, and is very small and delicate. It can be quite difficult to distinguish this nerve from the background tissue when the area about the thyroid gland is inflamed, as well as covered with blood following the initial incision. As the result, the risk of vocal cord damage or paralysis following thyroid surgery is very high, and also is quite serious in that it can result in the patient's complete loss of speech. Even if the laryngeal nerve has simply been stretched or bruised, the loss of speech may last for several months. In the unfortunate cases where the nerve is completely severed, the paralysis is permanent, and surgical attempts to repair the same have not yet proven successful.

The use of laryngeal electromyography with surface electrodes to locate the recurrent laryngeal nerve has proven successful, as discussed in U.S. Pat. No. 5,178,145 issued to Rea. But the types and sizes of electrodes available is limited. Most electrodes are self retaining in that they have some sort of "built in" means for insertion, such as a paddle or handle. Most electrodes are also fixed in size and may not be adaptable for use on all patients and in particular pediatric patients, small children, and in some cases small adults.

SUMMARY OF THE INVENTION

In general, the attachable and size adjustable surface electrode for laryngeal electromyography generally consists of a flexible plate having an anterior and a posterior surface specifically for insertion into the human laryngopharynx adjacent to the cricothyroideus muscles (the vocal cords). An electrical conductive plate is mounted on the anterior surface to provide an electric contact with the cricothyroideus muscles. An insulated wire extends from the electrical conductive plate for monitoring or delivering electrical pulses to the cricothyroideus muscles. There are graduations parallel to a center line on the electrical conductive plate for cutting and sizing the flexible plate and electrical conductive plate to the size of the patient's laryngopharynx. There is an adhesive material on the posterior surface of the flexible plate for attachment of the attachable and size adjustable surface electrode to an endotracheal tube, insert device, postcricoid paddle or other such device.

The principal object of the present invention is to provide an electrode and method for laryngeal electromyography to locate a recurrent laryngeal nerve, and in particular an electrode that can be directly attached to an endotracheal tube, insert device, postcricoid paddle or other such device, so it must be flexible and bendable, rather then being self retaining or permanently fixed to some sort of device for insertion.

Another object is to provide such an electrode and method for continuous intraoperative laryngeal nerve location monitoring during thyroid surgery.

Yet another object is to provide such an electrode and method that is easily attached to an insert device and thus easily inserted in the patient, and in particular small adults, children, and for use in pediatrics, and that is adapted for reliable operation.

Another object is to provide such an electrode and method that is simple and accurate in operation whereby surgeons without extensive experience in thyroid surgery may conduct the surgery, yet avoid damage to the laryngeal nerve.

Still another object is to provide such an electrode and method to allow monitoring of the cricothyroideus muscles, a muscle innervated by the recurrent laryngeal nerve, without resort to needle invasion of other laryngeal musculature.

Even another object is to provide such an electrode and method for accurately and securely placing the electrode through the pharynx (throat) into the patient's postcricoid space without interfering with other equipment.

And yet another object is to provide such an electrode that is economical to manufacture, efficient in use, and particularly well adapted for the proposed use.

Other objects and advantages of this invention will become apparent from the following description taken in connection with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

Figure 1:
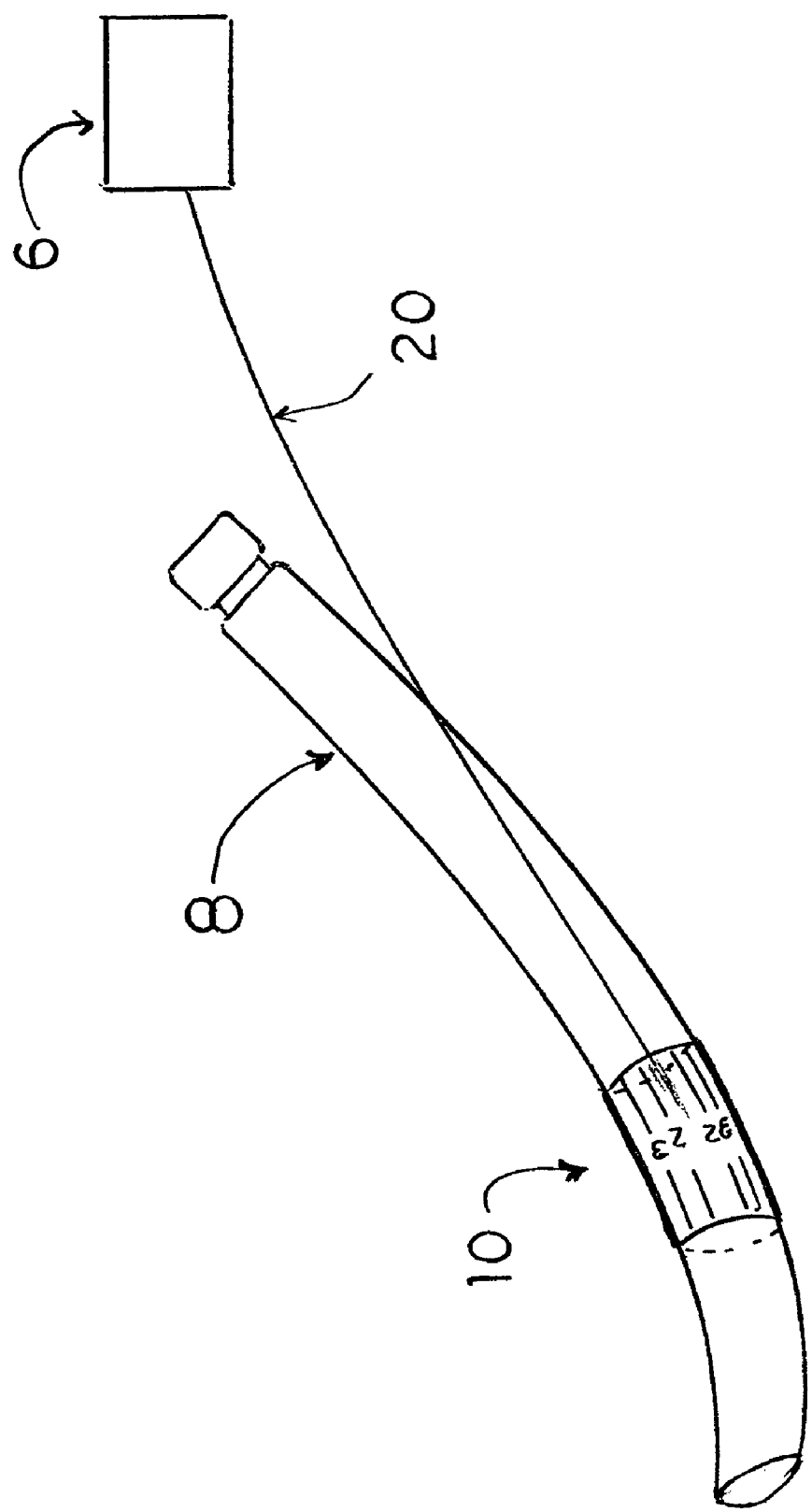
FIG. 1 is a perspective view of the primary embodiment of an attachable and size adjustable surface electrode for laryngeal electromyography embodying the present invention wrapped around and attached to an endotracheal tube.
Figure 2:
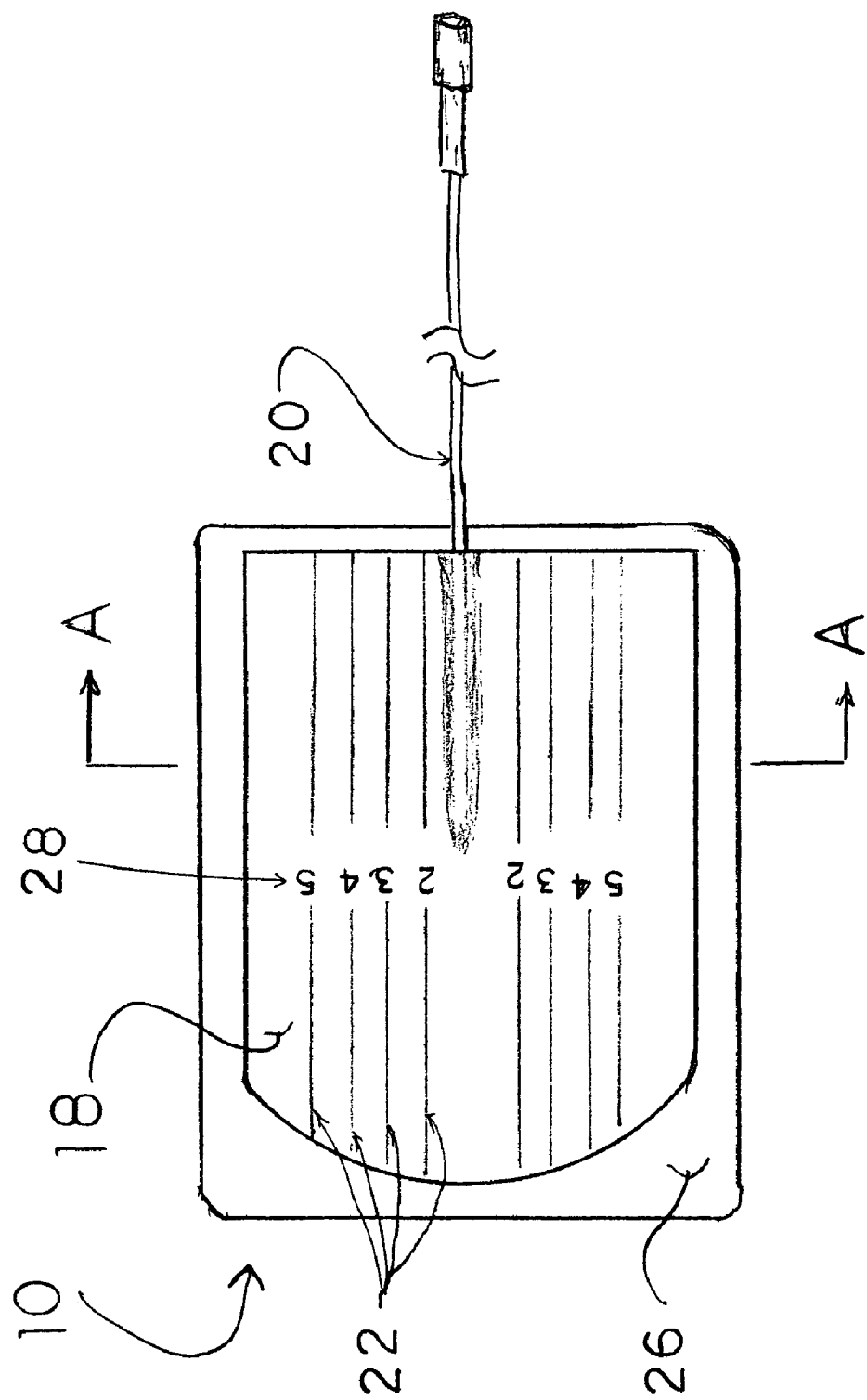
FIG. 2 is a top view of the primary embodiment of attachable and size adjustable surface electrode for laryngeal electromyography embodying the present invention.
Figure 2A:
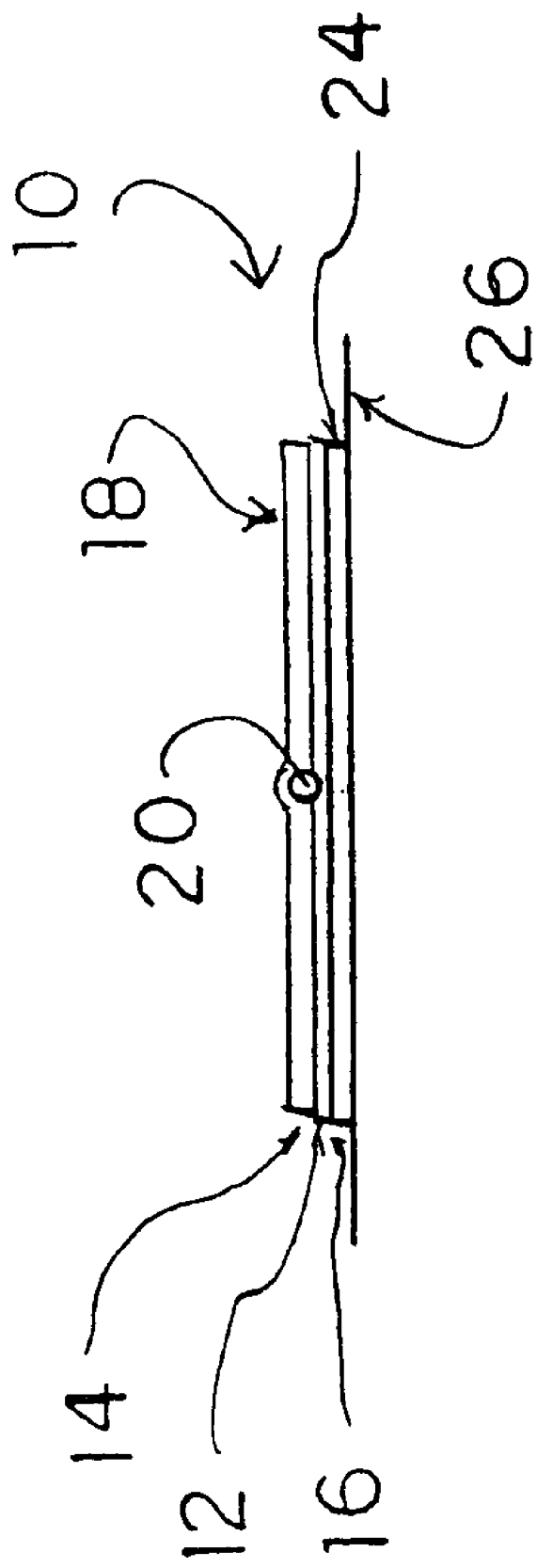
FIG. 2A is a cross sectional view of the attachable and size adjustable surface electrode as illustrated in FIG. 2.
Figure 3:
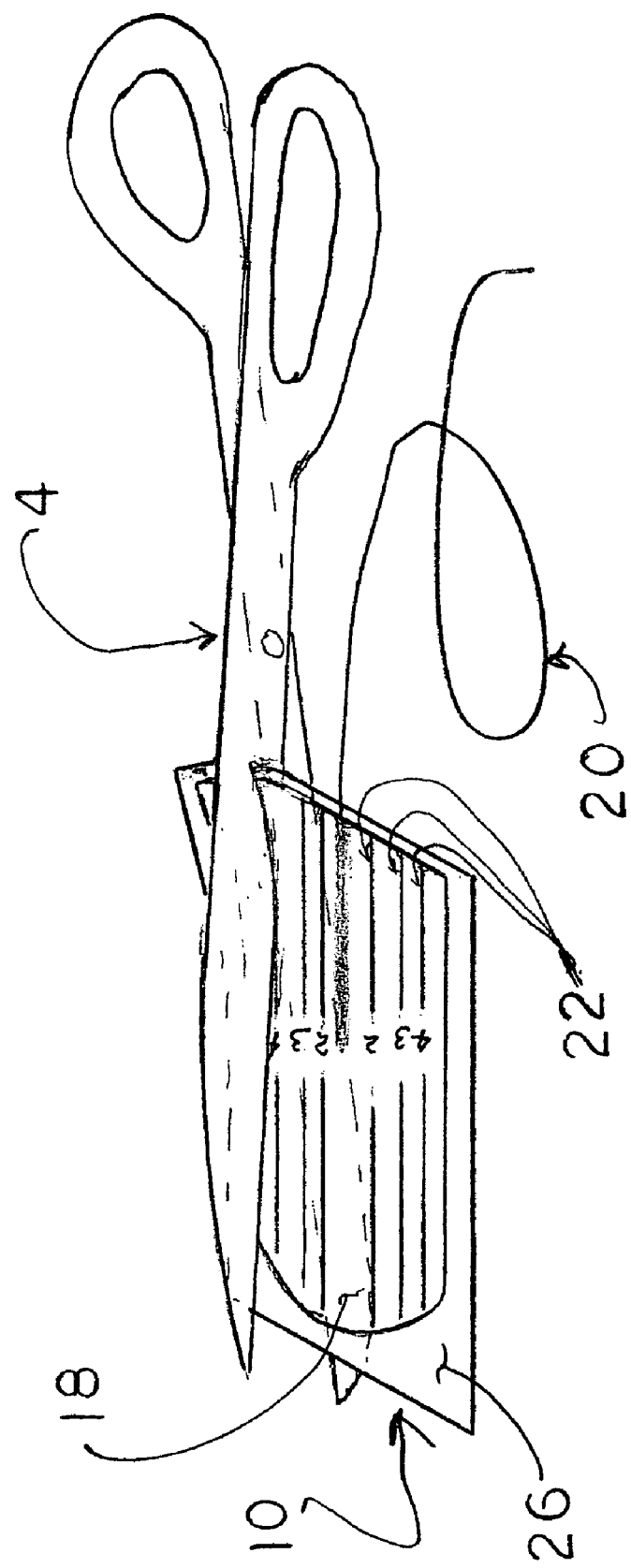
FIG. 3 shows the attachable and size adjustable surface electrode being trimmed or size adjusted by cutting with scissors.

Referring more in detail to the drawings, the detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and is a representative basis for teaching one skilled in the art to variously employ the present invention and virtually any appropriately detailed structure.

The reference numeral 10 generally designates the attachable and size adjustable surface electrode for laryngeal electromyography of the present invention. The attachable and size adjustable surface electrode 10 generally consists of a flexible plate 12 having an anterior surface 14 and a posterior surface 16 specifically for inserting in the human laryngopharynx adjacent to the cricothyroideus muscles (the vocal cords). An electrical conductive plate 18 is mounted on the anterior surface 14, to provide an electric contact with the cricothyroideus muscles. A wire 20 extends from the electrical conductive plate 18 for monitoring or delivering electrical pulses to the cricothyroideus muscles. The other end of the wire 20 is attachable to an electromyographic monitor. There are graduations 22 parallel to a center line marked on the electrical conductive plate 18, or posterior side 16 of the flexible plate 12, for cutting and sizing the flexible plate 12 and electrical conductive plate 18 to the size of the patient's laryngopharynx. There is an adhesive material 24 on the posterior surface 16 of the flexible plate 12 for attachment of the attachable and size adjustable surface electrode 10 to an endotracheal tube, insert device, postcricoid paddle or other such device 8.

No other known device is flexible and size adjusting by cutting, and attachable to an endotracheal tube, insert device, postcricoid paddle or other such device 8 by wrapping the attachable and size adjustable surface electrode 10 around the endotracheal tube, insert device, postcricoid paddle or other such device 8 and attaching via the adhesive 24.

The flexible plate 12 has an anterior surface 14 and a posterior surface 16 specifically for inserting in the human laryngopharynx adjacent to the cricothyroideus muscles (the vocal cords). The flexible plate 12 is made from a non-conductive material that is flexible and bendable so it can be wrapped about and attached to an endotracheal tube, insert device, postcricoid paddle, or other such device 8. It could be made from a variety of material, but the preferred embodiment it is made of a thin layer of polyethylene, foam polyethylene, or some other medical grade material. Typically, the initial dimensions are 24 millimeters (mm) in width and 45 mm in length in the preferred embodiment. However, different sizes and different materials can be made based upon the intended use, size of the patient, and by market forces.

The electrical conductive plate 18 is mounted on the anterior surface 14 of the flexible plate 12, to provide an electric contact with the cricothyroideus muscles. The electrical conductive plate 18 is constructed of a metallic conductive layer of silver ink, flexograph silver deposition, or similar electrically conductive medium. The electrical conductive plate 18 can be attached with the adhesive properties of the conductive material itself or it may be attached with silver loaded conductive adhesive, nonconductive acrylic resin, or other type of material or adhesive that adheres to both the electrical conductive plate 18 and the flexible plate 12. The dimensions of the electrical conductive plate 18 is somewhat smaller than the outer dimensions of the flexible plate 12. However, after the attachable and size adjustable surface electrode 10 is cut to size, the width of both will be approximately equal. Both the flexible plate 12 and electrical conductive plate 18 will be cut simultaneously so they should be the same width after sizing.

A wire 20 extends from the electrical conductive plate 18 for monitoring or delivering electrical pulses from/to the cricothyroideus muscles. One end of the wire 20 is in electrical contact with the electrical conductive plate 18. Preferably, the wire 20 is in electrical contact with the back side along a center line of the electrical conductive plate 18 between the flexible plate 12 and the electrical conductive plate 18. In this location the electrical contact is protected and provides a mechanically sound connection location. The wire 20 may be attached with silver loaded conductive adhesive or any other electrical conductive means. The other end of wire 20 is adapted for connection to an electrical signal receiver and monitor, such as an electromyographic monitor instrument 6. The wire 20 typically is a flexible conductive wire in the nature of 40 gauge more or less with an insulating covering. The wire 20 is very fine in the nature and with a length of approximately 6 inches or longer to facilitate threading the same into the patient's laryngopharynx. The main purpose of the wire 20 is to provide the input of electrical signals to or from electrical conductive plate 18 to an electromyographic monitor instrument 6. In this regard, any wire of any gauge or length fulfilling this purpose is within the scope of the invention.

There are a plurality of graduations 22 parallel to and on both sides of a center line on the electrical conductive plate 18, in the preferred embodiment. The graduations 22 are for cutting and sizing the flexible plate 12 and electrical conductive plate 18 to the size of the endotracheal tube or insert device 8 appropriate for the patient's laryngopharynx. The attachable and size adjustable surface electrode 10 is easily cut and sized using scissors 4 or some other cutting device. The graduations 22 could also be marked on the posterior surface 16 of the flexible plate 12 or back side of the removable plastic film or paper 26 in other embodiments, that are not shown. The graduations 22 are typically marked on one side of center in a spaced relationship to graduations 22 marked on the other side of center. This is so an equal amount can be cut off on each side of center. The graduations 22 may or may not be marked with alphanumerical characters 28 for ease of identifying corresponding graduation marks on the opposite sides of center. Typically, the graduations 22 and alphanumerical characters if any, can be marked with ink, paint, etching, stamping, or by any method that readily shows the graduations 22 and alphanumerical characters. Any means used for marking the graduation should be considered within the scope of the invention.

There is a non conductive adhesive material 24 on the posterior surface 16 of the flexible plate 12 for attachment of the attachable and size adjustable surface electrode 10 to an endotracheal tube, insert device, postcricoid paddle or other such device 8. In the preferred embodiment, the adhesive is covered with a thin film of plastic or paper 26. The thin plastic film is peeled off so the attachable and size adjustable surface electrode 10 can be wrapped around and attached via the adhesive to an endotracheal tube, insert device, postcricoid paddle or other such device 8. Any type of adhesive that functions to attach the attachable and size adjustable surface electrode 10 to an endotracheal tube, insert device, postcricoid paddle or other such device 8 is within the scope of the invention.

In use:

The first step is to determine the size of the patient's trachea and larynx and the type of insert device to be used. As used here an insert device 8 can be an endotracheal tube, insert device, postcricoid paddle, or other such device. The attachable and size adjustable surface electrode 10 is cut to size along graduations 22 using scissors 4 or some other cutting device. The adhesive backing is peeled off and the attachable and size adjustable surface electrode 10 is wrapped around and attached to the insert device 8.

The patient is then anesthetized and the insert device 8 with the attachable and size adjustable surface electrode 10 is inserted into the patient's mouth and into his trachea. The attachable and size adjustable surface electrode 10 is positioned between the vocal cords with the attachable and size adjustable surface electrode 10 making contact with the cricothyroideus muscles. The outer end of the wire 20 is attached to an electromyographic monitor 6. Typically, the insert device 8 has an opening longitudinally through the device to allow the patient to breathe.

The electromyographic monitor 6 generally is a device that will receive an electrical signal originating in the cricothyroideus muscles and transmitted thereto through the wire 20, and provide a display of the signal. The signal receiver and monitor may comprise an oscilloscope or the like, and is preferably a mechanism which provides an audible alarm upon receipt of the electrical signal, whereby the location of the recurrent laryngeal nerve can be determined while the surgeon maintains continuous sight observation of the area of surgery.

The electromyographic monitor 6 or signal generator typically includes a probe and provides means for applying an electrical signal to the recurrent laryngeal nerve 22. The signal is of a relatively low voltage, in the nature of five to forty volts, and is preferably a repetitive stimuli of low frequency, short pulses, in the nature of 4 pulses per second stimulation rate.

After the surgeon has made his initial incision, and is approaching the area of the recurrent laryngeal nerve, he simply applies the probe to the area in which he believes the nerve to be located. If the probe contacts the laryngeal nerve, the signal applied thereto by the signal generator 6 is transmitted through the laryngeal nerve to the cricothyroideus muscles which in turn is thereby excited. Excitement of the cricothyroideus muscles causes an electrical impulse to be generated therein and is transmitted through the electrical conductive plates 18 and the wire 20 to the signal receiver and monitor. The electrical conductive plate 20 serves as an electrical ground for the signal receiver and monitor. In the case of an audio monitor, the device shall emit popping sounds in a frequency which corresponds to the recognized warning tone emitted by signal receiver and monitor. The surgeon need only recognize the characteristic frequency of these popping sounds to know that he has located the recurrent laryngeal nerve. After having determined the location of the nerve, the surgeon can work very slowly and carefully in this area so as to insure the nerve is not injured.

The attachable and size adjustable surface electrode 10 may be removed from the patient by simply pulling on the insert device 8, thereby removing the insert device 8 and the attachable and size adjustable surface electrode 10 distally through the patient's mouth.

It is to be understood that while we have illustrated and described certain form of our invention, it is not to be limited to the specific forms or arrangements herein described and shown.

What is claimed is:

1. An attachable and size adjustable electrode for laryngeal electromyography comprising:

a flexible plate having an anterior and a posterior surface specifically for inserting in the human laryngopharynx adjacent to the cricothyroideus muscles (the vocal cords);

an electrical conductive plate mounted on the anterior surface of the flexible plate, to provide an electric contact with the cricothyroideus muscles;

a wire extending from the electrical conductive plate for monitoring or delivering electrical pulses;

graduations parallel to a center line marked on the electrical conductive plate or posterior surface of the flexible plate for cutting and sizing the flexible plate and electrical conductive plate to the size of the patient's laryngopharynx; and adhesive material on the posterior surface of the flexible plate, such that the flexible plate with the electrical conductive plate may be wrapped around an endotracheal tube, insert device, postcricoid paddle or other such device and attached thereto with the adhesive material.

2. The attachable and size adjustable electrode for laryngeal electromyography of claim 1 in which said electrical conductive plate is constituted for inserting and retaining adjacent to cricothyroideus muscles in the human laryngopharynx for continuous collection of electrical signals from the cricothyroideus muscles and adapted for purpose of connection to a signal monitor via said wire.

3. The attachable and size adjustable electrode for laryngeal electromyography of claim 1 further comprising alphanumerical characters to mark the graduations.

4. The attachable and size adjustable electrode for laryngeal electromyography of claim 1 in which the wire is attached to the electrical conductive plate between a back side of the electrical conductive plate and the anterior surface of the flexible plate.

5. The attachable and size adjustable electrode for laryngeal electromyography of claim 1 further comprising a plastic film or paper covering the adhesive material, the plastic film or paper being removable to expose the adhesive material for attachment of the attachable and size adjustable electrode to an insert device.

\* \* \* \* \*